(12) United States Patent
Skinner

(10) Patent No.: US 7,038,460 B1
(45) Date of Patent: May 2, 2006

(54) ELECTROSTATIC DUST DETECTOR

(75) Inventor: Charles H. Skinner, Lawrenceville, NJ (US)

(73) Assignee: The United States of America as represented by the United States Department of Energy, Washington, DC (US)

(*) Notice: Subject to any disclaimer, the term of this patent is extended or adjusted under 35 U.S.C. 154(b) by 45 days.

(21) Appl. No.: 10/787,220

(22) Filed: Feb. 27, 2004

(51) Int. Cl.
*G01N 27/62* (2006.01)
*G01N 27/00* (2006.01)

(52) U.S. Cl. .................. 324/464; 324/71.4
(58) Field of Classification Search ............. 324/464, 324/71.4, 76.16, 76.29
See application file for complete search history.

(56) References Cited

U.S. PATENT DOCUMENTS

| | | | | |
|---|---|---|---|---|
| 3,718,029 A | * | 2/1973 | Gourdine et al. | 73/28.02 |
| 4,338,568 A | * | 7/1982 | Frosch et al. | 324/466 |
| 5,457,396 A | * | 10/1995 | Mori et al. | 324/724 |
| 5,565,786 A | * | 10/1996 | Balousek | 324/718 |
| 6,043,639 A | * | 3/2000 | Arrowsmith et al. | 324/71.4 |
| 6,122,599 A | * | 9/2000 | Mehta | 702/100 |
| 6,169,394 B1 | * | 1/2001 | Frazier et al. | 324/71.4 |
| 6,204,656 B1 | * | 3/2001 | Cheiky-Zelina et al. | 324/71.4 |
| 6,664,492 B1 | * | 12/2003 | Babb et al. | 209/127.1 |

* cited by examiner

*Primary Examiner*—Anjan Deb
(74) *Attorney, Agent, or Firm*—Bradley W. Smith; Mark P. Dvorscak; Paul A. Gottlieb

(57) ABSTRACT

An apparatus for detecting dust in a variety of environments which can include radioactive and other hostile environments both in a vacuum and in a pressurized system. The apparatus consists of a grid coupled to a selected bias voltage. The signal generated when dust impacts and shorts out the grid is electrically filtered, and then analyzed by a signal analyzer which is then sent to a counter. For fine grids a correlation can be developed to relate the number of counts observed to the amount of dust which impacts the grid.

8 Claims, 6 Drawing Sheets

Circuit Diagram Including Power Supply, High Pass and Low Pass Filters, Oscilloscope Single Channel Analyzer and Counter.

Schematic of T3 Circuit; Trace Width 254 μm, Spacing 381 Microns, Overall Area 1.2 x 1.2 cm (Not to Scale).

Plot of Breakdown Voltages of Circuit Board Without Particles Present.

Circuit Diagram Including Power Supply, High Pass and Low Pass Filters, Oscilloscope Single Channel Analyzer and Counter.

Particle Delivery System for Experiments in Air. The Dimensions are in cm.

FIG. 4

Particle Delivery System for Experiments in Vacuum.

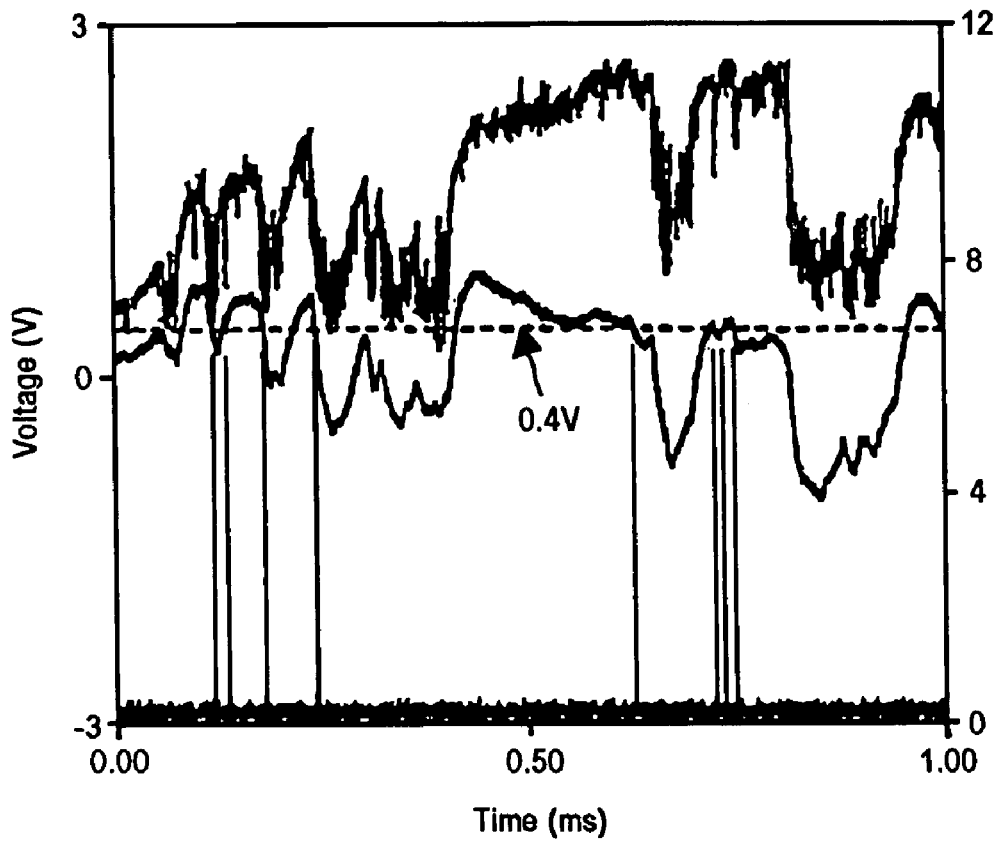

Typical Waveforms of the Signal Created by Approximately 0.3 mg of Impinging Particles on Grid T4 with a Bias Voltage of 50V in Air. The Uppermost Waveform is the Unfiltered Signal, the Waveform Directly Below it is the Signal after it Passed Through the Band Pass Filters (Y-Axis Scale on Left). The Lowermost Waveform is the Signal from the Signal Channel Analyzer (SCA) and Corresponding Y-Axis Scale is on the Right. Also Shown is a Dotted Line Indicating 0.4V. The SCA was Set to Trigger on the Falling Edges of Pulses at 0.4V.

FIG. 6

ELECTROSTATIC DUST DETECTOR

The United States Government has rights in this invention pursuant to Contract No. DE-AC02-76CH03073 between the U.S. Department of Energy and Princeton University.

FIELD OF THE INVENTION

This invention is an apparatus detecting the presence of dust in remote and potentially hazardous environments. The dust may be radioactive due to the presence of such elements such as tritium or other materials, it may have hazardous heavy metals and be toxic with the potential to be chemically reactive with steam or air.

BACKGROUND OF THE INVENTION

There is a developing need to be able to determine the presence of potentially hazardous dust on isolated surfaces. As noted above, this dust may be radioactive, chemically active under certain ambient conditions or toxic. One use for such a device would be in conjunction with the next generation fusion reactor which could produce a large amount of dust and possible ensuing safety hazards. For example, if beryllium dust is not constrained within set limits, explosions could occur in the presence of steam under certain conditions. Thus, a device is needed to detect dust on remote surfaces for future fusion reactors; however, such devices do not exist for hostile environments. The subject apparatus is an electrostatic device which provides a correlation between recorded counts and particle concentration. This leads to the object of this apparatus which is to measure the particle inventory in a wide range of environments including those where radioactive particles are present.

SUMMARY OF THE INVENTION

The subject apparatus provides a means of detecting dust and to a lesser degree to determine the particle concentration of the dust. The subject invention applies electrostatic principles to electrically conductive dust to determine the presence of dust. To arrive at this capability, a grid of electrically conducting traces was applied to a circuit board which was then energized. As the dust lands on the energized grid a short circuit is created as the conductive dust bridges the gap between adjacent traces which causes a change in the measured voltage. The results of the electrostatic measurements were used to determine a proximate correlation between the readings and the dust particle concentration. Typically, the dust particles vaporize in a few seconds restoring the initial voltage; however, in the case where a large quantity of particles created a continuous short, an external electrical circuit provides a signal indicating such an event is occurring. The apparatus can be operated over a given period of time to determine time related scenarios that lead to the generation of dust.

These and other objects of the present invention consist of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

FIG. 4 represents the particle delivery system for experiments in air. The dimensions are in cm.

FIG. 6 is a typical waveform of the signal created by approximately 0.3 mg of impinging particles on a grid with a bias voltage of 50 V in air.

DESCRIPTION OF PREFERRED EMBODIMENT

This invention capitalizes on the ability to employ a circuit board having a fixed, narrowly spaced charged grid to detect the presence of electrically conducting dust particles. This device is capable of operating in a hostile environment where other devices would prove to be ineffective or impractical.

Figure 1:
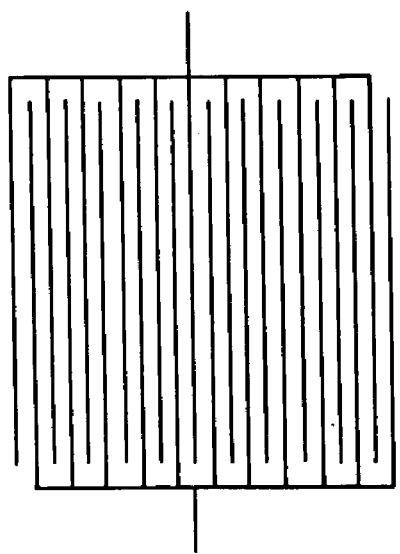
FIG. 1 is a schematic diagram of the circuit board with the applied traces.
Figure 2:
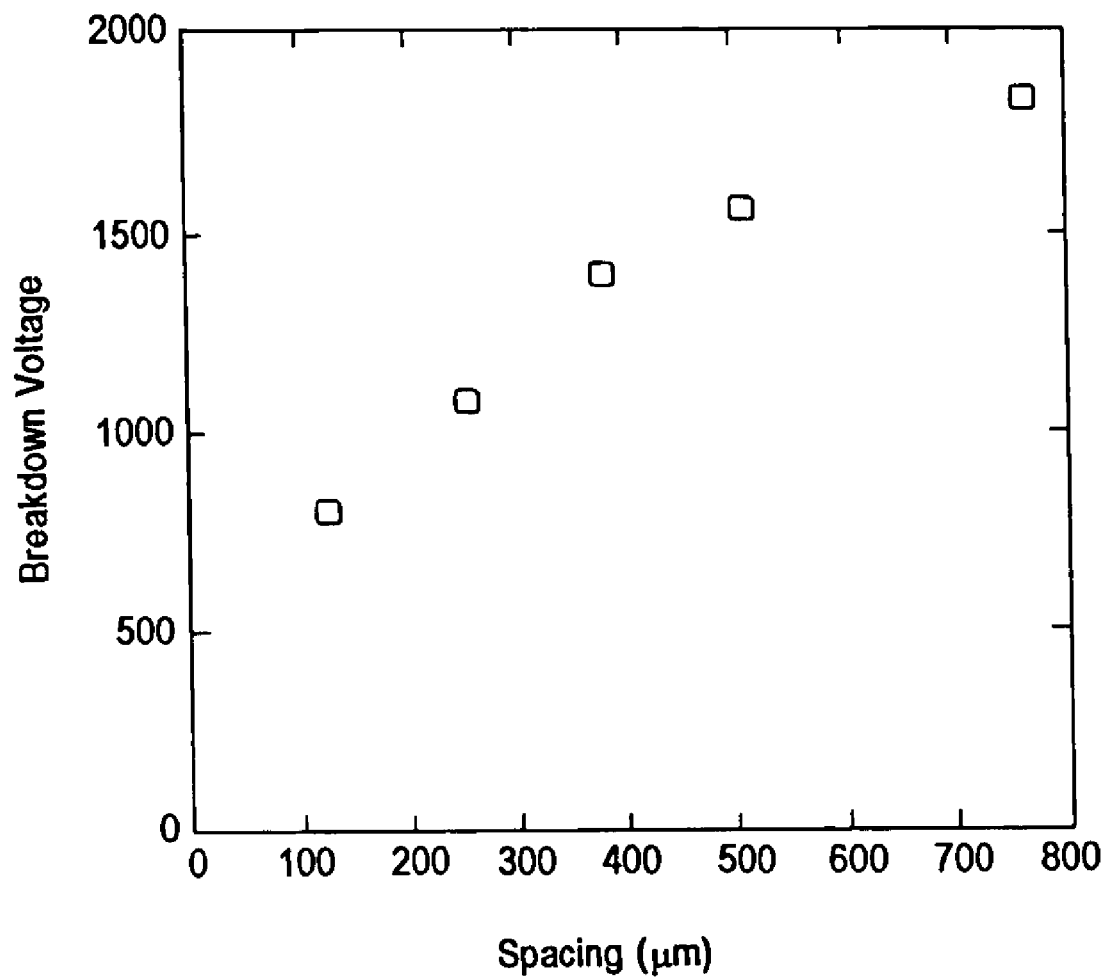
FIG. 2 is a diagram of the breakdown voltage of the traced circuit board without dust particles and as a function of the trace spacing.

The dust detection device employs a circuit board mounted grid to which a voltage potential has been applied for the detection of electrically conducting dust particles. A schematic of the grid is depicted in FIG. 1. The apparatus is triggered as the dust particles impact the grid and cause a transient short circuit to develop across certain elements of the grid. This creates a change in circuit conditions causing a current pulse which can be picked-up on circuit analyzing devices such as an oscilloscope or a counter coupled to an analyzer. Generally, the dust which causes the short circuit vaporizes within a few seconds.

Standard circuit board technology was used to deposit a grid, FIG. 1, of interlocking traces on the circuit board; however in a fusion reactor environment more rugged materials such as a ceramic substrate might be preferable. The boards were made of 0.56 mm thick Teflon® substrate with rolled 1-ounce copper. After etching the traces of the grid, tin plating 4–6 microns thick was applied over the copper by the immersion process. A variety of trace widths and trace spacings were used. The traces were 127 or 254 µm wide, separated by distances of 127 µm to 762 µm and covering an area of 1.2×1.2 cm.

To test the system typically cylindrical particles measuring between 10 to 500 µm in length and 1 to 20 µm in diameter were used to simulate the effect of dust on the grid. Some of the particles were large enough to bridge the gap between the traces as individual particles; however, often two or more adjoining particles were needed to create the short circuit. As noted earlier, the particles typically vaporized after a few seconds restoring the electrical circuit to its original configuration and restoring the original standoff voltage.

Figure 3:
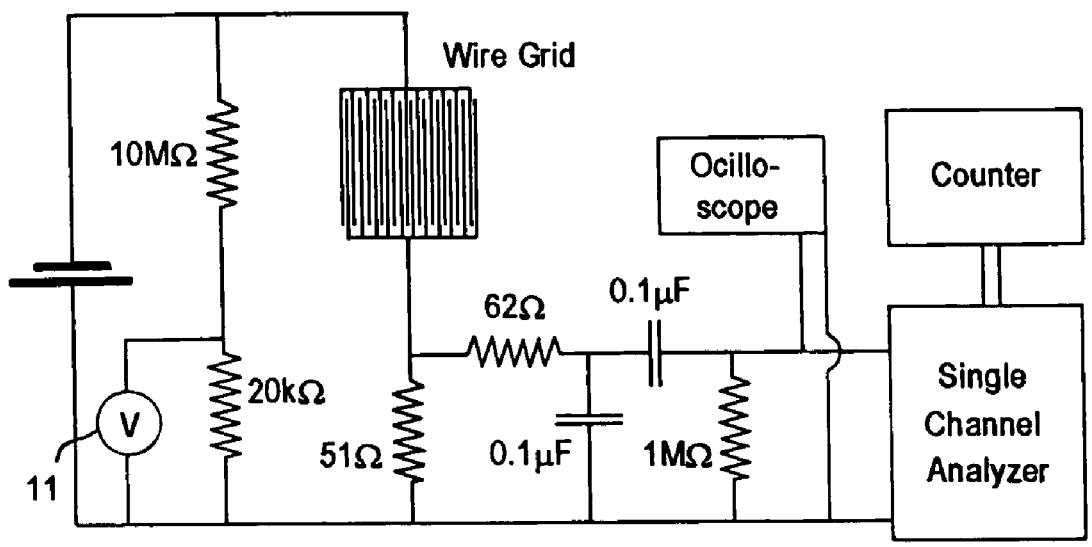
FIG. 3 is a circuit diagram including the power supply, the high and low pass filters, the oscilloscope, a single channel analyzer, voltmeter and a counter.
Figure 5:
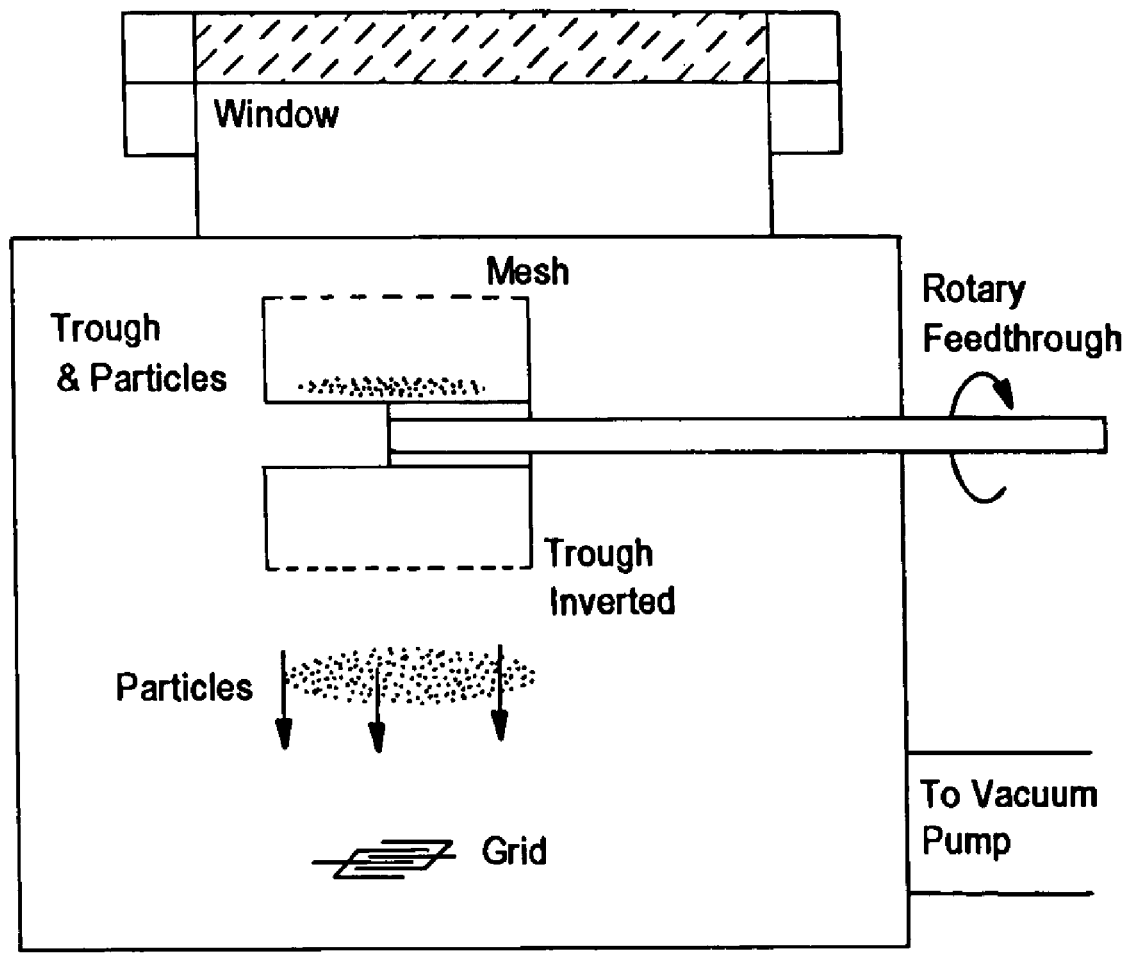
FIG. 5 represents the particle delivery system for experiments in a vacuum.

In order to detect the events initiated by the presence of the conductive dust particles, the electrical apparatus as shown in FIG. 3 was employed. A variable power supply, 12, supplied the bias voltage while a voltage divider, 14, across the output was used to monitor the output voltage. When a circuit is created by the impingement of dust on the grid, a current flow through the 51 ohm resistor, 16. This creates a signal which exhibits low and high frequency fluctuations and in some cases a continuing DC voltage. To produce a waveform suitable for counting, the signal was passed through a band-pass filter, 18, having a pass band of from 1.6 Hz to 25 kHz. This produced a waveform which was suitable for a single channel analyzer, 20, which was electrically coupled to a counter, 22. The single channel analyzer, 20, produced an output pulse every time the input signal decreased past a level of 400 mV which allowed the pulses to be counted by the counter, 22. The waveforms of the signal created by the impinging dust were also recorded on an oscilloscope, 24. FIG. 6 illustrates the wave form and the output pulses from the single channel analyzer.

To test the dust detection apparatus an experimental testing system was developed. The circuit board containing the grid was mounted 2 cm high on a 35 cm by 25 cm by 7.5 cm deep aluminum box. A 2.5 cm diameter pipe, FIG. 4, was used to deliver a controlled amount of particulate to the area of the grid. Care was taken to make the distribution of the particle as uniform as possible. A 7 mm hole, 32, was constructed in the top surface of the horizontal pipe, 34, to allow for the injection of a predetermined amount of particulate matter. The dust exit port, 36, was positioned 6 cm over the grid. A 10 scc/min stream of nitrogen gas was introduced through tube, 38, which had its exit port 3 cm upstream from the dust injection port, 32. This arrangement deposited particles in a circular area having a diameter of 10 cm and centered on the center of the grid.

In order to estimate the amount of dust incident on the grid, a collection bin having the same area as the grid was placed on the grid and the amount of dust reaching the grid was measured and compared to the amount of dust inputted through the injection hole, 32. The total mass of input particles ranged from 20 mg to 80 mg. The fraction of particles deposited in the bin ranged from 2–4% with a mean of 2.9% and a standard of deviation of 0.8%. In air, an operating voltage of 30 V was chosen since below this level the response became more variable due to the occurrence of more frequent continuous short circuits; in addition, the current was limited to below 200 mA to avoid damage to the traces. While in a vacuum, the voltage was in the range of from 30 v to 50 v and again the current was limited to below 200 mA. Employing these conditions, in air the short circuit created by the particle or particles was usually transient in nature resulting in the oxidation of the particles while under a vacuum, the particles were subject to sublimation so the detector was able to reset and detect particles continuously. The detection threshold for air was below 50 μg/cm$^2$ for a 127 μm grid spacing where 34 μg/cm$^2$ gave 25 counts for a single unit of blown dust. In a vacuum, the detection limit was somewhat higher. The upper detection limit for each grid was determined by a large quantity of particles creating a continuous short circuit. For the coarsest grid, 762 μm, this limit was above 1.6 mg/cm$^2$ For the fine grid spacing, a correlation was detected between the particle concentration and the recorded counts. Thus, grids of different spacing can be combined to extend the dynamic range of the device.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical applications and should enable others skilled in the art to utilize the invention in various embodiments and with various modifications as are suited to the particular use contemplated. It is intended that the scope of the invention be defined by the claims appended hereto.

We claim:

1. An apparatus for detecting electrically conducting dust particles on a surface exposed to an air or a vacuum environment comprising:

an electrically conducting detection grid having two or more interlocking tracing networks where each network has a plurality of tracings, where adjacent tracings have a specified separation or spacing and which in a dust free environment said grid represents an open circuit between adjacent tracings and where in an environment of settled dust an electrically conducting bridge of dust particles is established between adjacent tracings forming a electrical short which exits for a varying time duration;

an electrically nonconducting substrate which supports said grid and where said substrate is mounted on a specified, possibly isolated, fixed surface to detect a presence of conducting dust particles which have settled on said surface;

a power supply which is electrically coupled to said grid and which is sized to provide voltage sufficient to vaporize said dust particle bridge;

a means for detecting an electrical chance or a short across said grid tracings where said electrical change or short indicates the presence of electrically conducting dust particles on said surface.

2. The apparatus of claim 1 where said electrical change detection means includes a means for filtering a signal generated by a electrical change across said grid such as a voltage change.

3. The apparatus of claim 2 where said filter is a bandpass filter.

4. The apparatus of claim 2 where said filtered signal is inputted to a means for processing said signal.

5. The apparatus of claim 4 where said processing means includes a channel analyzer to which a counter is electrically coupled.

6. The apparatus of claim 4 where said processing means includes an oscilloscope.

7. The apparatus of claim 1 where said power supply is capable of providing a variable bias voltage across a plurality of traces which form said grid.

8. The apparatus of claim 1 where said trace specified separation or spacing is determined based on the expected dust particle size.

* * * * *